US00PP18161P2

(12) United States Plant Patent
Probst

(10) Patent No.: US PP18,161 P2
(45) Date of Patent: Oct. 30, 2007

(54) ***MISCANTHUS* PLANT NAMED 'SUPER STRIPE'**

(50) Latin Name: *Miscanthus sinensis*
Varietal Denomination: Super Stripe

(76) Inventor: Darrell R. Probst, 63 Williamsville Rd., Hubbardston, MA (US) 01452-1315

( * ) Notice: Subject to any disclaimer, the term of this patent is extended or adjusted under 35 U.S.C. 154(b) by 0 days.

(21) Appl. No.: 11/454,030

(22) Filed: Jun. 15, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Miscanthus* plant named 'Super Stripe', characterized by its relatively compact, upright to somewhat outwardly spreading plant habit; dense and bushy growth habit; vigorous growth habit; green-colored leaves with yellow green-colored bands; and good garden performance.

1 Drawing Sheet

Botanical designation: *Miscanthus sinensis.*
Cultivar denomination: 'Super Stripe'.

BACKGROUND OF THE INVENTION

The present invention relates to a new and distinct cultivar of *Miscanthus* plant, botanically known as *Miscanthus sinensis,* and hereinafter referred to by the name 'Super Stripe'.

The new *Miscanthus* is a product of a planned breeding program conducted by the Inventor in Avondale, Pa. The objective of the program is to create and develop new *Miscanthus* cultivars having good plant habit and unique leaf banding patterns.

The new *Miscanthus* originated from an open-pollination of the *Miscanthus sinensis* cultivar Zebrinus, not patented, as the female, or seed, parent with an unknown selection of *Miscanthus sinensis* as the male, or pollen, parent. The new *Miscanthus* was discovered and selected by the Inventor as a single plant within the progeny of the stated open-pollination in a controlled environment in Avondale, Pa. in 1983.

Asexual reproduction of the new *Miscanthus* by divisions in Lancaster, Pa. since 2000, has shown that the unique features of this new *Miscanthus* are stable and reproduced true to type in successive generations.

SUMMARY OF THE INVENTION

The cultivar Super Stripe has not been observed under all possible environmental conditions. The phenotype may vary somewhat with variations in environment such as temperature and light intensity, without, however, any variance in genotype.

The following traits have been repeatedly observed and are determined to be the unique characteristics of 'Super Stripe'. These characteristics in combination distinguish 'Super Stripe' as a new and distinct cultivar of *Miscanthus:*

1. Relatively compact, upright to somewhat outwardly spreading plant habit; dense and bushy growth habit.

2. Vigorous growth habit.
3. Green-colored leaves with yellow green-colored bands.
4. Good garden performance.

In side-by-side comparisons conducted in Lancaster, Pa., plants of the new *Miscanthus* differed from plants of the female parent, the cultivar Zebrinus, in the following characteristics:

1. Plants of the new *Miscanthus* were not upright and not as open as plants of the cultivar Zebrinus.
2. Plants of the new *Miscanthus* were shorter than plants of the cultivar Zebrinus.
3. Plants of the new *Miscanthus* had more yellow green-colored bands on the leaves than plants of the cultivar Zebrinus.

Plants of the new *Miscanthus* can be compared to plants of the *Miscanthus* cultivar Strictus, not patented. In side-by-side comparisons conducted in Lancaster, Pa., plants of the new *Miscanthus* differed from plants of the cultivar Strictus in the following characteristics:

1. Plants of the new *Miscanthus* were not as upright as plants of the cultivar Strictus.
2. Plants of the new *Miscanthus* were much shorter than plants of the cultivar Strictus.
3. Plants of the new *Miscanthus* had more yellow green-colored bands on the leaves than plants of the cultivar Strictus.

BRIEF DESCRIPTION OF THE PHOTOGRAPH

The accompanying photograph illustrates the overall appearance of the new *Miscanthus.* This photograph shows the colors as true as it is reasonably possible to obtain in colored reproductions of this type. Colors in the photograph may differ slightly from the color values cited in the detailed botanical description which accurately describe the colors of the new *Miscanthus.* The photograph comprises a side perspective view of typical two-year old plants of 'Super Stripe' grown in an outdoor nursery in Lancaster, Pa.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Pensacola, Fla. during the spring in an outdoor nursery and under conditions and practices which approximate those generally used in commercial *Miscanthus* production. During the production of the plants, day temperatures ranged from 21° C. to 35° C. and night temperatures ranged from 18° C. to 35° C. Measurements and numerical values for represent averages for typical six-month old plants grown in 10-cm containers.

Botanical classification: *Miscanthus sinensis* cultivar Super Stripe.

Parentage:

*Female, or seed, parent.*—*Miscanthus sinensis* cultivar Zebrinus, not patented.

*Male, or pollen, parent.*—Unknown selection of *Miscanthus sinensis,* not patented.

Propagation:

*Type.*—By divisions.

*Time to produce a rooted young plant, summer.*—About 70 days at 35° C.

*Time to produce a rooted young plant, winter.*—About 77 days at 18° C.

*Root description.*—Thick; white in color.

Plant description:

*Plant form/growth habit.*—Relatively compact; upright and somewhat outwardly spreading plant habit; dense and bushy growth habit. Vigorous growth habit.

*Plant height.*—About 45 cm.

*Plant diameter or spread.*—About 34 cm.

*Culm (stem) description.*—Shape: Cylindrical; enclosed by leaf sheaths. Length: About 15 cm. Diameter: About 5 mm. Internode length: About 2.5 cm. Aspect: Upright. Strength: Strong. Texture: Smooth, glabrous. Color: Close to 144A to 144C.

Foliage description:

*Arrangement.*—Alternate, two-ranked, simple; leaf base sheathing the culm.

*Length (including sheath).*—About 38 cm.

*Width.*—About 1 cm.

*Shape.*—Linear.

*Apex.*—Tapering to a point.

*Margin.*—Entire with short bristles; bristles inconspicous.

*Aspect.*—Initially upright then outwardly arching with development.

*Texture, upper and lower surfaces.*—Smooth, glabrous; lower surface slightly glaucous.

*Venation pattern.*—Parallel.

*Color.*—Developing foliage, upper and lower surfaces: Green ground color, close to 144A; yellow green bands, ranging from close to 144B to 154D. Fully expanded foliage, upper and lower surfaces: Green ground color, close to 146A to 147A; yellow green bands, ranging from close to 144B to 154D; midvein, close to 146A to 147A; secondary veins, similar to lamina.

*Ligule (located at point of contact with culm).*—Length: About 2 mm. Diameter: About 3 mm. Texture, inner surface: Pubescent. Texture, outer surface: Smooth, glabrous. Color, inner and outer surfaces: Close to 154D.

Inflorescence description: Inflorescence and flower development has not been observed on plants of the new *Miscanthus.*

Disease/pest resistance: Plants of the new *Miscanthus* have not been shown to be resistant to pathogens and pests common to *Miscanthus.*

Garden performance: Plants of the new *Miscanthus* have been observed to have good garden performance and tolerate wind, rain and temperatures ranging from about −23° C. to about 41° C.

It is claimed:

1. A new and distinct *Miscanthus* plant named 'Super Stripe' as illustrated and described.

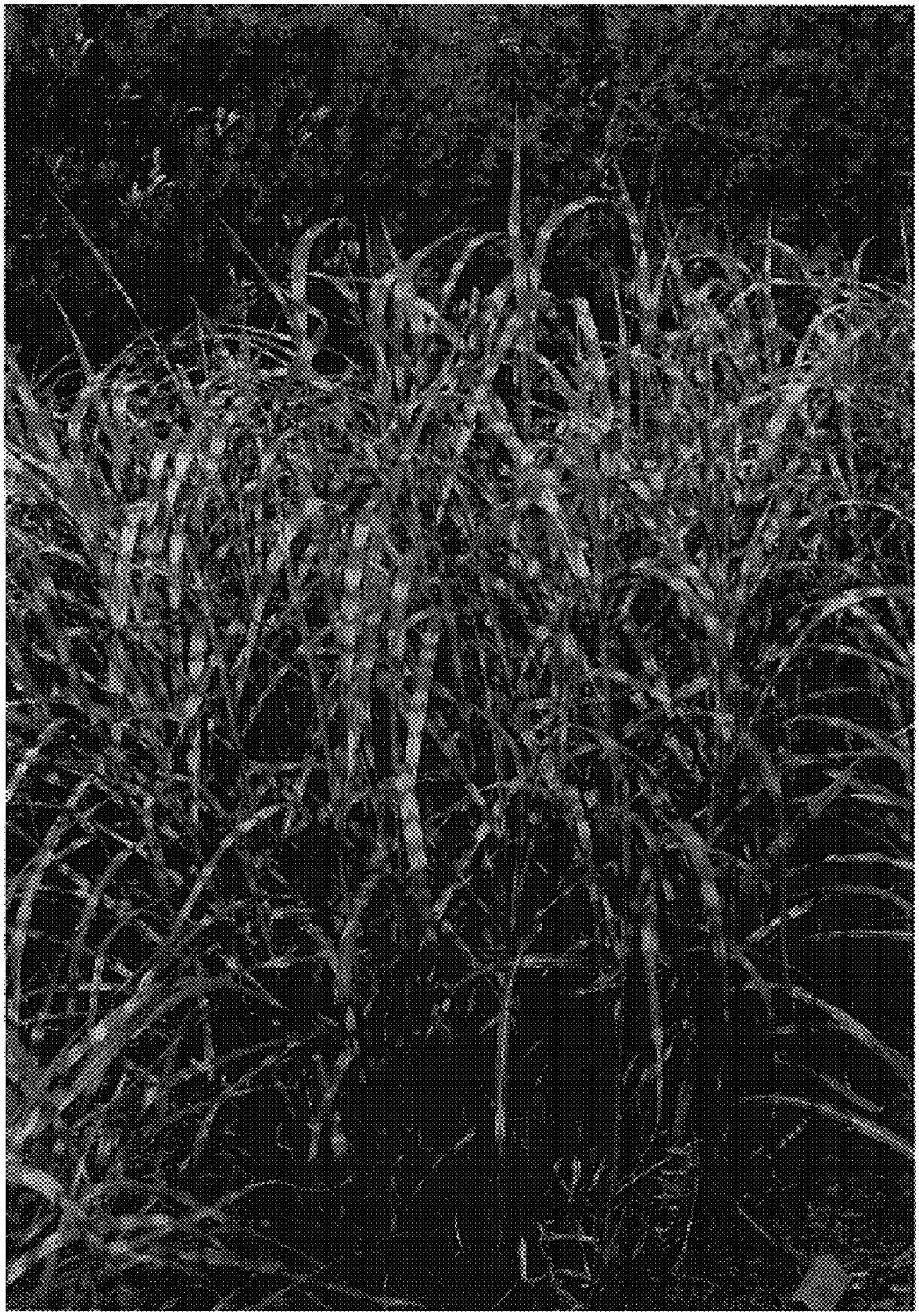

* * * * *